(12) United States Patent
Tabuchi et al.

(10) Patent No.: US 8,435,965 B2
(45) Date of Patent: May 7, 2013

(54) COMPOSITION FOR SOFT CONTACT LENS AND ADSORPTION SUPPRESSING METHOD

(75) Inventors: Nobuhito Tabuchi, Tokyo (JP); Manabu Hattori, Tokyo (JP)

(73) Assignee: Lion Corporation, Tokyo (JP)

( * ) Notice: Subject to any disclaimer, the term of this patent is extended or adjusted under 35 U.S.C. 154(b) by 545 days.

(21) Appl. No.: 12/097,471

(22) PCT Filed: Dec. 25, 2006

(86) PCT No.: PCT/JP2006/325751
§ 371 (c)(1),
(2), (4) Date: Jun. 13, 2008

(87) PCT Pub. No.: WO2007/077783
PCT Pub. Date: Jul. 12, 2007

(65) Prior Publication Data
US 2009/0176737 A1    Jul. 9, 2009

(30) Foreign Application Priority Data

Dec. 27, 2005  (JP) .................................. 2005-375234
Oct. 13, 2006  (JP) .................................. 2006-279411

(51) Int. Cl.
*A61K 31/724* (2006.01)
*A61K 31/728* (2006.01)

(52) U.S. Cl.
USPC .......................................................... 514/54

(58) Field of Classification Search ........................ None
See application file for complete search history.

(56) References Cited

U.S. PATENT DOCUMENTS

| 5,438,060 | A | * | 8/1995 | Miyazaki et al. ........... 514/262.1 |
| 5,998,488 | A | | 12/1999 | Shinohara et al. |

FOREIGN PATENT DOCUMENTS

| JP | 2001-002563 A | 1/2001 |
| JP | 2001-122774 A | 3/2001 |
| JP | 2001-158734 A | 6/2001 |
| JP | 2001-158750 A | 6/2001 |
| JP | 2001-318350 A | 11/2001 |
| JP | 2002-249445 A | 9/2002 |
| JP | 2002-322048 A | 11/2002 |
| JP | 2003-002837 A | 1/2003 |
| JP | 2003-252800 A | 9/2003 |
| JP | 2004-002364 A | 1/2004 |
| JP | 2004-359679 A | 12/2004 |
| JP | 2005-037928 A | 2/2005 |
| JP | 2005-84558 A | 3/2005 |
| JP | 2005-104970 A | 4/2005 |
| JP | 2006-312627 A | 11/2006 |
| JP | 2006-312628 A | 11/2006 |
| WO | 01/89578 A1 | 11/2001 |

OTHER PUBLICATIONS

Kiyobayashi ,JP 2005-084558, Mar. 31, 2005, machine translation and partial human translation.*
Kiyobayashi, JP 2005-084558, Mar. 31, 2005, human translation of tables.*
Banker (1996, Modern Pharmaceutics, pp. 516-518.*
Masson et al. WO 01/89578, Nov. 29, 2001, machine translation.*
European Search Report for application No. 06843155, dated Nov. 9, 2009.
Fridriksdottir et al., "Formulation and Testing of Methazolamide Cyclodextrin Eye Drop Solutions", Journal of Controlled Release, vol. 44, 1997, pp. 95-99, Elsevier Science Ireland Ltd.
Zepelin® Tengan'eki Tenpu Bunsho, Kowa Co., Ltd., 2005 Nen 9 Gatsu.

* cited by examiner

*Primary Examiner* — Layla Bland
(74) *Attorney, Agent, or Firm* — Birch, Stewart, Kolasch & Birch, LLP

(57) ABSTRACT

Disclosed is a composition for soft contact lenses which enables to suppress adsorption of a basic chemical substance onto a soft contact lens. This composition for soft contact lenses comprises (A) a basic chemical substance selected from amines having a secondary amino group and/or a tertiary amino group and salts thereof, and (B) one or more substances selected from amino acids and salts thereof, acid mucopolysaccharides and salts thereof and cyclodextrin, while having a pH of 3.5 to 4.8. Also disclosed is a method for suppressing adsorption of the basic chemical substance onto a soft contact lens.

14 Claims, No Drawings

COMPOSITION FOR SOFT CONTACT LENS AND ADSORPTION SUPPRESSING METHOD

TECHNICAL FIELD

This invention relates to a composition for soft contact lenses including a basic chemical substance selected from amines containing a secondary amino group and/or a tertiary amino group and salts thereof, and also to a method for suppressing adsorption of the basic chemical substance above-stated on a soft contact lens.

BACKGROUND ART

When soft contact lenses are worn, the lens surface tends to be getting dry and be deposited with pollen and pollutant substances that may cause allergic symptoms such as itchiness, inflammatory hyperemia and the like. Accordingly, there has been long demanded a composition for users of soft contact lenses, which contains an anti-inflammatory component, an antihistamine component or an anti-hyperemic component.

For the anti-inflammatory, antihistamine or anti-hyperemic component, there are known basic compounds containing a secondary amino group and/or a tertiary amino group. These basic chemical substances have high affinity for soft contact lenses, so that when used as a composition for users of soft contact lens, they have the possibility of being adsorbed on the lens surface and accumulated inside the lens as time passes, thus giving an adverse influence on the physical properties and the usability during wear of the lenses and also on the side effect thereof in some cases. In order to allow adaptation for the use of soft contact lenses, it is essential to suppress the basic chemical substance from being adsorbed on the lens.

Several methods of suppressing adsorption of chemical substances on a soft contact lens have been hitherto proposed including a method of suppressing adsorption of lipid soluble vitamins with a polymeric compound and a nonionic surface active agent (see Patent Document 1: Japanese Patent Laid-Open No. 2001-158734) and a method of suppressing adsorption of dipotassium glycyrrhizinate with an amino acid or the like (see Patent Document 2: Japanese Patent Laid-Open No. 2001-2563). However, ophthalmic compositions for suppressing adsorption, on soft contact lenses, of such a basic chemical substance as set out above have never been developed yet. Although there are known a method of suppressing adsorption of chlorpheniramine maleate on a container while controlling a pH of the composition to 5 to 6 (see Patent Document 3: Japanese Patent Laid-Open No. 2002-249445) and a method of suppressing adsorption on a container by formulating cyclodextrin (see Patent Document 4: Japanese Patent Laid-Open No. 2004-359679), no method of suppressing adsorption on soft contact lenses has been known. It is to be noted that prior art literatures related to the present invention are mentioned below.

Patent Document 1:
Japanese Patent Laid-Open No. 2001-158734
Patent Document 2:
Japanese Patent Laid-Open No. 2001-2563
Patent Document 3:
Japanese Patent Laid-Open No. 2002-249445
Patent Document 4:
Japanese Patent Laid-Open No. 2004-359679
Patent Document 5:
Japanese Patent Laid-Open No. 2002-322048
Patent Document 6:
Japanese Patent Laid-Open No. 2001-122774
Patent Document 7:
Japanese Patent Laid-Open No. 2004-2364
Patent Document 8:
Japanese Patent Laid-Open No. 2003-252800
Patent Document 9:
Japanese Patent Laid-Open No. 2001-158750
Patent Document 10:
Japanese Patent Laid-Open No. 2003-2837

DISCLOSURE OF THE INVENTION

Problem to be Solved by the Invention

The invention has been made under such circumstances. And an object of the present invention is to provide a composition for soft contact lenses which is able to suppress a basic chemical substance selected from amines having a secondary amino group and/or a tertiary amino group and salts thereof from being adsorbed on a soft contact lens. The invention also has as its object the provision of a method for suppressing adsorption of the basic chemical substance on soft contact lenses.

Means for Solving the Problems

We made intensive studies in order to achieve the above objects and, as a result, found that when an amino acid or a salt thereof such as potassium L-aspartate or the like, an acidic mucopolysaccharide or a salt thereof such as sodium chondroitin sulfate or the like, or a cyclodextrin is incorporate into a composition for soft contact lenses including a basic chemical substance selected from amines having a secondary amino group and/or a tertiary amino group and salts thereof and a pH of the composition is adjusted to 3.5 to 4.8, the basic chemical substance is suppressed from being adsorbed on a soft contact lens, thus arriving at completion of the invention.

Accordingly, the following inventions are provided.
[1] A composition for soft contact lenses comprising
(A) a basic chemical substance selected from amines containing a secondary amino group and/or a tertiary amino group and salts thereof, and
(B) at least one compound selected from the group consisting of amino acids and salts thereof, acidic mucopolysaccharides and salts thereof, and cyclodextrins, and said composition having a pH of 3.5 to 4.8.
[2] The composition for soft contact lenses as recited in [1] above, wherein the component (A) is at least one basic chemical substance selected from the group consisting of epinephrine, ephedrine, methylephedrine, naphazoline, phenylephrine, neostigmine, diphenhydramine, chlorpheniramine, tetrahydrozoline, pranoprofen, diclofenac, Allantoin, ketotifen, acitazanolast, levocabastine, amlexanox, ibudilast, pemirolast, lomefloxacin, ofloxacin, norfloxacin, gentamicin, sisomycin, micromycin, oxybuprocaine, distigmine, timolol, carteolol, betaxolol, dipivefrine, pilocarpine, pirenoxine, cyclopentolate, tropicamide, and salts thereof.
[3] The composition for soft contact lenses s recited in [1] or [2], wherein the amino acid and salt thereof are selected from the group consisting of L-glutamic acid, epsilon-aminocaproic acid, L-aspartic acid and salts thereof.
[4] The composition for soft contact lenses as recited in any one of [1] to [3] above, wherein the acidic mucopolysaccharide and salt thereof are selected from the group consisting of a chondroitin sulfate, a chondroitin polysulfate, hyaluronic acid and salts thereof.

[5] The composition for soft contact lenses as recited in any one of [1] to [4], wherein the cyclodextrin is selected from the group consisting of α-cyclodextrin, β-cyclodextrin and γ-cyclodextrin.

[6] The composition for soft contact lenses as recited in any one of [1] to [5], further comprising a monoterpenoid compound and/or a sesquiterpenoid compound.

[7] The composition for soft contact lenses as recited in any one of [1] to [6], further comprising at least one buffer selected from the group consisting of a boric acid buffer, an acetic acid buffer, a phosphoric acid buffer, a carbonic acid buffer, a citric acid buffer and trometamol.

[8] The composition for soft contact lenses as recited in any one of [1] to [7], wherein the composition is an ophthalmic solution, a solution for wearing contact lenses, a solution for removing contact lenses or a care agent for contact lenses.

[9] A method for suppressing adsorption of a basic chemical substance on a soft contact lens comprising incorporating at least one compound selected from the group consisting of amino acids and salts thereof, acidic mucopolysaccharides and salts thereof, and cyclodextrins into a composition of soft contact lenses including a basic chemical substance selected from the group consisting of amines having a secondary amino group and/or a tertiary amino group and salts thereof.

BENEFITS OF THE INVENTION

According to the invention, in a composition for soft contact lenses which includes a basic chemical substance selected from amines having a secondary amino group and/or a tertiary amino group and salts thereof, the suppression of adsorption of the basic chemical substance on a soft contact lens can be achieved.

BEST MODE FOR CARRYING OUT THE INVENTION

The composition for soft contact lenses of the invention comprehends ophthalmic compositions employed for soft contact lens users under conditions of contact between the composition and a soft contact lens (solutions for wearing, ophthalmic solutions, solutions for removing and the like) and soft contact lens care agents (cleaning agents, antiseptic solutions, rinsing agents, preservatives, moistening agents, such multipurpose compositions as mentioned above, and the like).

The component (A) of the invention is a basic chemical substance selected from amines having a secondary amino group and/or a tertiary amino group and salts thereof, for which mention is made of an anti-inflammatory component, an antihistamic component, an anticongestive component or the like. Specific examples of the amines having a secondary amino group and/or a tertiary amino group and salts thereof include epinephrine, ephedrine, methylephedrine, naphazoline, phenylephrine, neostigmine, diphenhydramine, chlorpheniramine, tetrahydrozoline, pranoprofen, diclofenac, allantoin, ketotifen, acitazanolast, levocabastine, amlexanox, ibudilast, pemirolast, lomefloxacin, ofloxacin, norfloxacin, gentamicin, sisomycin, micromycin, oxybuprocaine, distigmine, timolol, carteolol, betaxolol, dipivefrine, pilocarpine, pirenoxine, cyclopentolate, tropicamide, and salts thereof. More specifically, there are mentioned epinephrine hydrochloride, ephedrine hydrochloride, methylephedrine hydrochloride, naphazoline hydrochloride, phenylephrine hydrochloride, neostigmine methylsulfate, diphenhydramine hydrochloride, chlorpheniramine maleate, tetrahydrozoline hydrochloride, ketotifen fumarate, levocabastine hydrochloride, pilocarpine hydrochloride and the like. These basic chemical substances may be used singly or in appropriate combination of two or more. Of these, chlorpheniramine maleate, diphenhydramine hydrochloride, tetrahydrozoline hydrochloride, naphazoline hydrochloride and neostigmine methylsulfate are preferred because a significant adsorption suppressing effect under the configuration of the invention can be attained.

The amount of the component (A) is preferred in the range of 0.001 to 1.0 w/v % (meaning weight/volume % (g/100 ml) herein and whenever it appears hereinafter) in the composition for soft contact lenses, more preferably 0.001 to 0.2 w/v %, further more preferably 0.002 to 0.1 w/v % and most preferably 0.005 to 0.1 w/v %.

The component (B) of the invention is one or more of those selected from amino acids and salts thereof, acidic mucopolysaccharides and salts thereof and cyclodextrins. The incorporating of the component (B) into the composition for soft contact lenses containing the basic chemical substance (A) enables the basic chemical substance (A) to be suppressed from adsorption on a soft contact lens. Of the components (B), an acidic mucopolysaccharide and a salt thereof are preferred because of lessened irritation at a low pH.

The preferred amino acids and salts thereof include L-glutamic acid, epsilon aminocaproic acid, L-aspartic acid and salts thereof (salts of alkali metals such as Na, K and the like, and ammonium salts). Specific examples include L-glutamic acid, epsilon aminocaproic acid, L-aspartic acid, sodium L-glutamate, potassium L-aspartate, magnesium L-aspartate, potassium magnesium L-aspartate and salts thereof. They may be used singly or in appropriate combination of two or more. Of these, L-glutamic acid and L-glutamates are preferred because of lessened irritation to eyes when applied as a low pH composition.

The acidic mucopolysaccharides and salts thereof include chondroitin sulfate, chondroitin polysulfate, hyaluronic acid and salts thereof (salts of alkali metals such as Na, K and the like and ammonium salts), heparin, keratosulfate and the like, which may be used singly or in appropriate combination of two or more. Of these, chondroitin sulfate, chondroitin polysulfate, hyaluronic acid and salts thereof are preferred.

Cyclodextrins include α-cyclodextrin, β-cyclodextrin, γ-cyclodextrin, δ-cyclodextrin and the like, which may be used singly or in appropriate combination of two or more. Of these, α-cyclodextrin, β-cyclodextrin and γ-cyclodextrin are preferably used.

When the amino acid and a salt thereof are used, the amount of the amino acid and its salt is preferably 0.01 to 3 w/v %, more preferably 0.025 to 1 w/v %, in the composition for soft contact lenses. If the amount is smaller, the effect of suppressing adsorption of the basic chemical substance on a soft contact lens may become unsatisfactory in some case. Over 3 w/v %, usability may lower.

When the acidic mucopolysaccharide and a salt thereof are used, the amount of the acidic mucopolysaccharide and its salt is preferably 0.01 to 1 w/v %, more preferably 0.025 to is 0.5 w/v % in the composition for soft contact lenses. If the amount is smaller, the effect of suppressing adsorption of the basic chemical substance on a soft contact lens may become unsatisfactory in some case. Over 1 w/v %, a viscous feeling may be shown after use.

When the cyclodextrin is used, the amount of the cyclodextrin is preferably 0.01 to 3 w/v %, more preferably 0.05 to 1 w/v %, in the composition for soft contact lenses. If the amount is smaller, the effect of suppressing adsorption of the basic chemical substance on a soft contact lens may become unsatisfactory in some case. Over 3 w/v %, solubility may become worsened.

It is preferred to incorporate a monoterpenoid compound and/or a sesquiterpenoid compound into the composition for soft contact lenses of the invention. Essential oils containing these compounds may also be used. More particularly, examples include camphor, cool mint No. 71212, geraniol, mint water, menthol, borneol, eucalyptus oil, fennel oil, bergamot oil, linalool, N-ethyl-p-menthane-carboxyamide (e.g., WS-3, made by Takasago International Corporation) and the like. The amount of these compounds is preferably 0.0001 to 0.1 w/v % in the composition for soft contact lenses. Moreover, the amount made in the range of 0.0005 to 0.03 w/v % is more preferred because of an effect of mitigating an irritation.

Further, a buffering agent is preferably incorporate into the composition for soft contact lenses of the invention. Examples of the buffering agent include one or two or more of those selected from boron-based buffering agents such as boric acid, borax and the like, acetic acid-based buffering agents such as acetic acid, sodium acetate, potassium acetate and the like, phosphoric acid-based buffering agents such as sodium hydrogen phosphate, sodium dihydrogen phosphate, potassium dihydrogen phosphate and the like, carbonic is acid-based buffering agents such as sodium carbonate, sodium hydrogen carbonate and the like, citric acid-based buffering agents such as citric acid, sodium citrate and the like, and trometamol. Of these, trometamol and the boron-based buffering agents such as boric acid, borax and the like are preferred. From the standpoint of the preservative efficacy, boric acid, trometamol or a mixture of boric acid-trometamol (boric acid and trometamol used in combination) is more preferred.

When the buffering agent is used, the amount is preferably 0.01 to 2 w/v %, more preferably 0.001 to 1 w/v % and further more preferably 0.05 to 0.5 w/v %, in the composition for soft contact lenses. If the amount is smaller, the stability of pH may not be maintained. Over 2 w/v %, the buffer power becomes so intense that an irritation may be felt in a low pH region.

Further, Q represented by the following equation as indicating a buffer power is preferably at 18 ml or below. Within this range, there can be obtained a composition whose irritation is low. More preferably, the value is at 14 ml or below. The lower limit of Q is preferably at least 5 ml. At smaller than 5 ml, the pH stability of the composition for soft contact lenses may become unsatisfactory in some cases.

$$Q = QHCl + QNaOH$$

(wherein QHCl: an amount (ml) of 0.1 mol/l of HCl necessary for lowering 100 g of a composition to a pH of 3.5, and QNaOH: an amount (ml) of 0.1 mol/l of NaOH necessary for raising 100 g of a composition to a pH of 7.5)

pH Measuring temperature (20° C.)

The pH (20° C.) of the composition for soft contact lenses of the present invention is 3.5 to 4.8, preferably 3.5 to 4.5, more preferably 3.6 to 4.0, further more preferably 3.6 to 3.9 and most preferably 3.7 to 3.8. If the pH is too small, an irritation may become intense. Over 4.8, the effect of suppressing adsorption of the basic chemical substance on an ionic soft contact lens becomes unsatisfactory. The measurement of pH is carried out by use of a pH osmometer (HOSM-1, made by DKK-Toa Corporation). The pH adjuster includes, for example, sodium hydroxide, potassium hydroxide, hydrochloric acid or the like. These may be used singly or in combination of two or more. From the standpoint of providing a composition whose preservative power is good, the pH should be low and is preferably at 3.9 or below, and when the pH is 3.5 to 3.9 and Q represented by the above equation is at 18 ml or below, it is possible to obtain a composition for soft contact lenses which is excellent in preservation efficacy and low in irritation to eyes if not containing an irritative preservative.

The composition of the invention for soft contact lenses may be further incorporated, if necessary, with various types of ingredients employed in eye washes within ranges not impeding the effect of the invention. Preferable ingredients include chemical substances other than the component (A), stabilizers, lubricants, tonicity agents, solubilizing adjuvants, antioxidants, preservatives, cooling agents and the like. These may be used singly or in combination of two or more.

The chemical substances other than the component (A) include, for example, anti-inflammatory agents such as dipotassium glycyrrhizinate, berberine chloride, berberine sulfate, sodium azulenesulfonate, zinc sulfate, zinc lactate, lysozyme hydrochloride and the like, vitamins such as flavin adenine dinucleotide sodium (activated vitamin $B_2$), cyanocobalamin (vitamin $B_{12}$), pyridoxine hydrochloride (vitamin $B_6$), vitamin E acetate, panthenol, calcium pantothenate, sodium pantothenate, retinol acetate, retinol palmitate (vitamin A palmitate) and the like, amino acids such as L-aminoethylsulfonic acid (taurine) and the like, sugars such as glucose, D-mannitol, xylitol and the like, sulfa drugs such as sulfamethoxazole, sodium sulfamethoxazole, sulfisoxazole, sodium sulfisoxizine and the like, antiallergic agents such as cromoglycic acid, sodium cromoglycate, tranilast and the like, tear adjuvant ingredients such as potassium chloride, sodium chloride and the like.

From the standpoint of the blockade of orbital fatigue and/or inflammatory caused by wearing of contact lens, it is preferred to use vitamins or derivatives thereof, antiinflamatory agents, tear adjuvant ingredients.

The amounts of drug substances other than the component (A) are so selected as to be effective amounts of the respective substances and are preferably 0.001 to 5 w/v % in the composition for soft contact lenses from the standpoint of an irritation to eyes and the stability of the composition.

Examples of the stabilizer include sodium edetate, edetic acid and the like. Edetic acids have the effect of maintaining the stability of the composition by the chelating action. The amount of the stabilizer is preferably 0.003 to 2 w/v % in the composition for soft contact lenses.

The lubricants include, for example, cellulose-based polymers such as methyl cellulose, hydroxypropylmethyl cellulose, hydroxyethyl cellulose and the like, polyvinyl-based polymer compounds such as polyvinylpyrrolidone, polyvinyl alcohol and the like, liquid paraffin, carboxyvinyl polymer, polyethylene glycol and the like. The amount of the lubricant is preferably 0.005 to 3 w/v % in the composition for soft contact lenses.

The tonicity agents include, for example, potassium chloride, sodium chloride, glycerine and the like. The amount of the tonicity is preferably of 0.005 to 3 w/v % in the composition for soft contact lenses.

The solubilizing adjuvants include, for example, surface active agents including polyhydric alcohols such as propylene glycol, polyethylene glycol, sorbitol and the like, POE sorbitan fatty acid esters such as Polysorbate 80, poloxamers, POE(20) sorbitan monooleate and the like, POE-hardened castor oils such as POE(60)-hardened castor oil. The amount of the solubilizing adjuvant is preferably 0.001 to 3 w/v % in the composition for soft contact lenses.

The antioxidants include, for example, dibutylhydroxytoluene (BHT), butylhydroxyanisole (BHA), hydroquinone, propyl gallate, sodium sulfite and the like. The amount of the antioxidant is preferably within 0.001 to 1 w/v % in the composition for soft contact lenses.

The preservatives include, for example, benzalkonium chloride, benzethonium chloride, chlorhexidine gluconate, sorbic acid, potassium sorbate, chlorobutanol, parabens such as paraoxy benzoic acid esters, and the like. The amount of the preservative is preferably within a range of 0.001 to 0.5 w/v % in the composition for soft contact lenses.

The balance of the composition of the invention for soft contact lenses is water and the composition can be prepared by a known manufacturing process. For instance, the respective components set out above are dissolved in water such as sterilized purified water, ion-exchanged water or the like, or in a mixed solvent with an alcohol such as ethanol, followed by adjusting the pH to 3.5 to 4.8 by means of a pH adjuster. If necessary, osmotic pressure is adjusted by means of tonicity agent. The thus obtained composition is charged in a known eyedropper (which is preferably one that contains a UV protecting agent or a dye therein in view of the stability of comprised ingredients) and packed with a film package or the like, thereby providing a composition for soft contact lenses whose storage stability is good.

The composition of the invention for soft contact lenses can be used as an ophthalmic solution for soft contact lens users, which is employed during the wear of soft contact lenses, a solution for wearing for soft contact lens, which is employed upon wear of soft contact lenses, a removing solution for soft contact lenses, which is employed upon removal of soft contact lenses, a care agent for contact lenses, an MPS (washing, rinsing, sterilization and preservation) for soft contact lenses, and the like. Of these, the composition is preferably provided as an ophthalmic solution for soft contact lens users, a solution for wearing for soft contact lens, a removing solution for soft contact lenses, and a care agent for contact lenses.

The type of soft contact lenses to which the composition of the invention for soft contact lenses is applicable is not critical and the composition can be used not only for a soft contact lens used repeatedly, but also for a one-day disposable soft contact lens, a one-week disposable soft contact lens and a two-week disposable contact lens.

The composition of the invention for soft contact lenses has the effect of suppressing adsorption of a basic chemical substance having a secondary amino group or a tertiary amino group on a soft contact lens. Therefore, the composition of the invention is suitable for a composition for suppressing adsorption of the basic chemical substance on a soft contact lens. Moreover, there can be provided a method for suppressing adsorption of a basic chemical substance on a soft contact lens comprising incorporating at least one compound selected from the group consisting of amino acids and salts thereof, acidic mucopolysaccharides and salts thereof, and cyclodextrins into a composition of soft contact lenses including a basic chemical substance selected from the group consisting of amines having a secondary amino group and/or a tertiary amino group and salts thereof.

EXAMPLES

Examples and Comparative Examples are given below for further illustrating the invention, but they are not construed as limiting the invention thereto.

Examples 1 to 108, Comparative Examples 1 to 4

Compositional (formulation unit; w/v %) components indicated in Tables 1 to 18 were dissolved in sterilized purified water, after which the respective solutions were aseptically filtered to prepare compositions (test solutions) for soft contact lenses. The thus obtained compositions were individually subjected to measurement of pH (20° C.), followed by the following test 1. The results are also shown in Tables 1 to 18.

Test 1: Test of Suppressing Adsorption of a Basic Chemical Substance (Basic Chemical Substance Adsorption Test on a Soft Contact Lens: n=3)

From four groups of soft contact lenses defined by FDA (Food and Drug Administration of the United States), there were used, as typical lenses, four types of lenses including "SeeQuence™" (made by Bausch & Lomb Japan), "Seed 14UV" (made by Seed Inc.), "Hi-Flow Ace" (made by Hoya Corporation), and "ACUVUE®" (made by Johnson and Johnson K.K.). One lens was immersed in 5 ml of a composition for soft contact lenses at 37° C. for 7 days, and an amount of the basic chemical substance in the residual solution was quantitatively determined by liquid chromatography. A composition for soft contact lenses in which no lens was immersed was similarly treated to provide a control. From a ratio to an amount of the basic chemical substance in the control, an adsorption ratio (%) of a basic chemical substance for four types of lenses was calculated according to the following equation:

$$[(\text{amount of a basic chemical substance in the control} - \text{an amount of the basic chemical substance in the residual solution})/\text{amount of the basic chemical substance in the control} \times 100].$$

Three measurements against one composition for soft contact lenses were carried out for every four types of lenses. The results are summarized such that an average adsorption ratio for every types of lens was calculated and a maximum adsorption ratio selected among the average adsorption ratios of the respective lenses was shown. And evaluation was shown according to the following evaluation standards. It will be noted that where two or more of basic chemical substances are contained, a maximum average adsorption ratio is selected among average adsorption ratios of all the basic chemical substances and shown.

(Evaluation Standards of Suppressing Adsorption on Soft Contact Lenses)

⊚: a maximum average adsorption ratio among average adsorption ratios (for every type of lens) of a basic chemical substance on a lens is less than 3%.

○: a maximum average adsorption ratio among average adsorption ratios (for every type of lens) of a basic chemical substance on a lens ranges from 3% to less than 5%.

Δ: a maximum average adsorption ratio among average adsorption ratios (for every type of lens) of a basic chemical substance on a lens ranges from 5% to less than 7%.

X: a maximum average adsorption ratio among average adsorption ratios (for every type of lens) of a basic chemical substance on a lens is not less than 7%.

Examples 109 to 137, Comparative Examples 5 and 6

Compositional (formulation unit: w/v %) components indicated in Tables 19 to 23 were dissolved in sterilized purified water, after which the respective solutions were aseptically filtered to prepare compositions (test solutions) for soft contact lenses. The thus obtained compositions were individually subjected to measurement of pH (20° C.), followed by the following tests 2 and 3. The results are also shown in Tables 19 to 23.

Test 2: Evaluation on Usability

Eye drops of a test solution were administered to ten soft contact lens users under conditions of wearing soft contact lenses to evaluate the usability under the following standards (the presence or absence of irritation).

<Evaluation Standards>
5: no irritation
4: little irritation
3: slight degree of irritation
2: moderate degree of irritation
1: high degree of irritation The results are indicated as ⊚ at an average point of 4 or over, ○ at 3 to less than 4, Δ at 2 to less than 3, and X at less than 2.

Test 3: Titration Test (Q Value)

100 g of each composition for soft contact lenses was weighed and titrated with 0.1 mol/l of HCl so as to lower the pH to 3.5, followed by measurement of an amount of 0.1 mol/l of HCl (QHCl) necessary therefor.

Separately, 100 g of the composition for soft contact lenses was weighed and titrated with 0.1 mol/l of NaOH so as to raise the pH to 7.5, followed by measurement of an amount of 0.1 mol/l of NaOH (QNaOH) necessary therefor.

The following equation is calculated using values obtained:

$$Q = QHCl + QNaOH.$$

It will be noted that the pH was measured at 20° C.

TABLE 1

| Composition (w/v %) | Example 1 | Example 2 | Example 3 | Example 4 | Example 5 | Comparative Example 1 | Comparative Example 2 |
|---|---|---|---|---|---|---|---|
| Chlorpheniramine maleate | 0.03 | 0.03 | 0.03 | 0.03 | 0.03 | 0.03 | 0.03 |
| Allantoin | 0.1 | 0.1 | 0.1 | 0.1 | 0.1 | 0.1 | 0.1 |
| Boric acid | 0.4 | 0.4 | 0.4 | 0.4 | 0.4 | 0.4 | 0.4 |
| EDTA | 0.003 | 0.003 | 0.003 | 0.003 | 0.003 | 0.003 | 0.003 |
| Potassium chloride | 0.6 | 0.6 | 0.6 | 0.6 | 0.6 | 0.6 | 0.6 |
| Sodium glutamate | 0.1 | 0.1 | 0.1 | 0.1 | 0.1 | | 0.1 |
| Propylene glycol | 0.8 | 0.8 | 0.8 | 0.8 | 0.8 | 0.8 | 0.8 |
| l-menthol | 0.009 | 0.009 | 0.009 | 0.009 | 0.009 | 0.009 | 0.009 |
| d-Borneol | 0.001 | 0.001 | 0.001 | 0.001 | 0.001 | 0.001 | 0.001 |
| pH adjuster (HCl/NaOH) | appropriate amounts | | | | | | |
| Total | 100.0 | | | | | | |
| pH | 4.7 | 4.5 | 4.0 | 3.8 | 3.5 | 3.8 | 5.0 |
| Suppression of adsorption of a basic chemical substance | Δ | ○ | ⊚ | ⊚ | ⊚ | Δ | X |
| Adsorption ratio (%) | 5.6 | 4.0 | 2.9 | 2.2 | 2.1 | 6.3 | 7.5 |

TABLE 2

| Composition (w/v %) | Example 6 | Example 7 | Example 8 | Example 9 |
|---|---|---|---|---|
| Chlorpheniramine maleate | 0.03 | 0.03 | 0.03 | 0.03 |
| Allantoin | 0.1 | 0.1 | 0.1 | 0.1 |
| Boric acid | 0.4 | 0.4 | 0.4 | 0.4 |
| EDTA | 0.05 | 0.05 | 0.05 | 0.05 |
| Potassium chloride | 0.1 | 0.1 | 0.1 | 0.1 |
| Sodium chloride | 0.3 | 0.3 | 0.3 | 0.3 |
| Sodium glutamate | 0.001 | 0.02 | 0.05 | 0.2 |
| Propylene glycol | 0.8 | 0.8 | 0.8 | 0.8 |
| l-menthol | 0.009 | 0.009 | 0.009 | 0.009 |
| d-Borneol | 0.001 | 0.001 | 0.001 | 0.001 |
| pH adjuster (HCl/NaOH) | appropriate amounts | | | |
| Total | 100.0 | | | |
| pH | 3.8 | 3.8 | 3.8 | 3.8 |
| Suppression of adsorption of a basic chemical substance | Δ | ○ | ⊚ | ⊚ |
| Adsorption ratio (%) | 5.3 | 3.9 | 2.8 | 2.3 |

TABLE 3

| Composition (w/v %) | Example 10 | Example 11 | Example 12 | Example 13 | Example 14 | Example 15 | Example 16 | Example 17 |
|---|---|---|---|---|---|---|---|---|
| Chlorpheniramine maleate | 0.03 | 0.03 | 0.03 | 0.03 | 0.03 | 0.03 | 0.03 | 0.03 |
| Boric acid | 0.4 | 0.4 | 0.4 | 0.4 | 0.4 | 0.4 | 0.4 | 0.4 |
| EDTA | 0.05 | 0.05 | 0.05 | 0.05 | 0.05 | 0.05 | 0.05 | 0.05 |
| Potassium chloride | 0.6 | 0.6 | 0.6 | 0.6 | 0.6 | 0.6 | 0.6 | 0.6 |
| Sodium chloride | 0.3 | 0.3 | 0.3 | 0.3 | 0.3 | 0.3 | 0.3 | 0.3 |
| Sodium glutamate | | | | | 0.05 | 0.05 | | |
| Potassium L-aspartate | 0.05 | | | | | 0.05 | 0.05 | |
| Epsilon aminocaproic acid | | 0.05 | | | | | | |
| Sodium chondroitin sulfate | | | 0.05 | | 0.05 | | 0.05 | |
| α-Cyclodextrin | | | | 0.05 | | | | |
| Sodium hyaluronate | | | | | | | | 0.05 |
| Propylene glycol | 0.8 | 0.8 | 0.8 | 0.8 | 0.8 | 0.8 | 0.8 | 0.8 |
| l-menthol | 0.009 | 0.009 | 0.009 | 0.009 | 0.009 | 0.009 | 0.009 | 0.009 |
| dl-Camphor | 0.001 | 0.001 | 0.001 | 0.001 | 0.001 | 0.001 | 0.001 | 0.001 |
| pH adjuster (HCl/NaOH) | Appropriate amounts | | | | | | | |
| Total | 100.0 | | | | | | | |
| pH | 3.8 | 3.8 | 3.8 | 3.8 | 3.8 | 3.8 | 3.8 | 3.8 |
| Suppression of adsorption of a basic chemical substance | ⊚ | ⊚ | ○ | ○ | ⊚ | ⊚ | ⊚ | ⊚ |
| Adsorption ratio (%) | 2.7 | 2.5 | 3.3 | 4.5 | 2.5 | 2.3 | 2.0 | 2.9 |

TABLE 4

| Composition (w/v %) | Example 18 | 19 | 20 | 21 | 22 | Comparative Example 3 | 4 |
|---|---|---|---|---|---|---|---|
| Chlorpheniramine maleate | 0.03 | 0.03 | 0.03 | 0.03 | 0.03 | 0.03 | 0.03 |
| Allantoin | 0.1 | 0.1 | 0.1 | 0.1 | 0.1 | 0.1 | 0.1 |
| Sodium chondroitin sulfate | 0.5 | 0.5 | 0.5 | 0.5 | 0.5 | | 0.5 |
| Trometamol | 0.003 | 0.003 | 0.003 | 0.003 | 0.003 | 0.003 | 0.003 |
| Boric acid | 0.2 | 0.2 | 0.2 | 0.2 | 0.2 | 0.2 | 0.2 |
| EDTA | 0.003 | 0.003 | 0.003 | 0.003 | 0.003 | 0.003 | 0.003 |
| Potassium chloride | 0.1 | 0.1 | 0.1 | 0.1 | 0.1 | 0.1 | 0.1 |
| Sodium chloride | 0.3 | 0.3 | 0.3 | 0.3 | 0.3 | 0.3 | 0.3 |
| Propylene glycol | 0.8 | 0.8 | 0.8 | 0.8 | 0.8 | 0.8 | 0.8 |
| l-menthol | 0.009 | 0.009 | 0.009 | 0.009 | 0.009 | 0.009 | 0.009 |
| d-Borneol | 0.001 | 0.001 | 0.001 | 0.001 | 0.001 | 0.001 | 0.001 |
| pH adjuster (HCl/NaOH) | | | appropriate amounts | | | | |
| Total | | | 100.0 | | | | |
| pH | 4.7 | 4.5 | 4.0 | 3.8 | 3.5 | 3.8 | 5.0 |
| Suppression of adsorption of a basic chemical substance | Δ | ○ | ◎ | ◎ | ◎ | Δ | X |
| Adsorption ratio (%) | 5.9 | 4.8 | 2.9 | 2.1 | 2.0 | 6.9 | 7.6 |

TABLE 5

| Composition (w/v %) | Example 23 | 24 | 25 | 26 | 27 | 28 |
|---|---|---|---|---|---|---|
| Chlorpheniramine maleate | 0.03 | 0.03 | 0.03 | 0.03 | 0.03 | 0.03 |
| Allantoin | 0.1 | 0.1 | 0.1 | 0.1 | 0.1 | 0.1 |
| Sodium chondroitin sulfate | 0.001 | 0.02 | 0.05 | 0.2 | 0.5 | 1 |
| Boric acid | 0.2 | 0.2 | 0.2 | 0.2 | 0.2 | 0.2 |
| EPTA | 0.05 | 0.05 | 0.05 | 0.05 | 0.05 | 0.05 |
| Potassium chloride | 0.1 | 0.1 | 0.1 | 0.1 | 0.1 | 0.1 |
| Sodium chloride | 0.3 | 0.3 | 0.3 | 0.3 | 0.3 | 0.3 |
| Propylene glycol | 0.8 | 0.8 | 0.8 | 0.8 | 0.8 | 0.8 |
| l-menthol | 0.009 | 0.009 | 0.009 | 0.009 | 0.009 | 0.009 |
| d-Borneol | 0.001 | 0.001 | 0.001 | 0.001 | 0.001 | 0.001 |
| pH adjuster (HCl/NaOH) | | | Appropriate amounts | | | |
| Total | | | 100.0 | | | |
| pH | 3.8 | 3.8 | 3.8 | 3.8 | 3.8 | 3.8 |
| Suppression of adsorption of a basic chemical substance | Δ | ○ | ◎ | ◎ | ◎ | ◎ |
| Adsorption ratio (%) | 5.5 | 4.2 | 2.9 | 2.7 | 2.5 | 2.3 |

TABLE 6

| Composition (w/v %) | Example 29 | 30 | 31 | 32 | 33 | 34 |
|---|---|---|---|---|---|---|
| Potassium L-aspartate | 0.1 | 0.1 | 0.1 | 0.1 | 0.1 | 0.1 |
| Magnesium L-aspartate | | | | | | |
| Sodium chondroitin sulfate | 0.5 | 0.5 | 0.5 | 0.5 | 0.5 | 0.5 |
| Chlorpheniramine maleate | 0.03 | 0.03 | 0.03 | 0.02 | 0.02 | 0.01 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | 0.005 | | 0.1 | |
| Pyridoxine hydrochloride | | 0.1 | 0.1 | | 0.1 | |
| Panthenol | | | | | | 0.1 |
| Tocopherol acetate | 0.05 | | | | | |
| Sodium cromoglycate | | | | | | 0.1 |
| Sodium hyaluronate | | 0.02 | | 0.02 | | 0.02 |
| Boric acid | 0.4 | 0.8 | | | | 0.4 |
| Borax | | 0.06 | | | | |
| Sodium hydrogen phosphate | | | 1 | | 1 | |
| Sodium dihydrogen phosphate | | | | | 0.2 | |
| Potassium dihydrogen phosphate | | | 0.2 | | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | 0.1 | | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | | 0.1 | 0.1 |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | | 0.002 | | |
| pH adjuster (HCl/NaOH) | | | Appropriate amounts | | | |
| Total | | | 100.0 | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 7

| Composition (w/v %) | Example 35 | 36 | 37 | 38 | 39 | 40 | 41 |
|---|---|---|---|---|---|---|---|
| Potassium L-aspartate | 0.1 | | | | | | |
| Magnesium L-aspartate | | 0.1 | 0.1 | 0.1 | 0.1 | 0.1 | 0.1 |
| Sodium chondroitin sulfate | 0.25 | 0.5 | 0.5 | 0.5 | 0.5 | 0.5 | 0.5 |
| Chlorpheniramine maleate | | 0.03 | 0.03 | 0.03 | 0.02 | 0.02 | 0.01 |

TABLE 7-continued

| Composition (w/v %) | Example 35 | 36 | 37 | 38 | 39 | 40 | 41 |
|---|---|---|---|---|---|---|---|
| Epinephrine hydrochloride | | 0.001 | | | | | |
| Ephedrine hydrochloride | | | 0.05 | | | | |
| Methylephedrine hydrochloride | | | | 0.05 | | | |
| Phenylepherine hydrochloride | | | | | 0.001 | | |
| Diphenhydramine hydrochloride | | | | | | 0.05 | |
| Tetrahydrozoline hydrochloride | 0.005 | 0.005 | | 0.005 | | 0.005 | |
| Naphazoline hydrochloride | | | 0.003 | | 0.003 | | 0.003 |
| Neostigmine methylsulfate | | | | 0.005 | | | 0.005 |
| Allantoin | | 0.1 | 0.1 | 0.1 | 0.1 | 0.1 | 0.1 |
| Zinc sulfate | | 0.1 | 0.1 | | 0.1 | | 0.1 |
| Zinc lactate | | | | 0.1 | | | |
| Lysozyme chloride | | | | | | 0.1 | |
| Retinol palmitate | | 0.01 | | | 0.005 | | |
| Pyridoxine hydrochloride | | | 0.1 | 0.1 | | 0.1 | |
| Panthenol | | | | | | | 0.1 |
| Tocopherol acetate | | 0.05 | | | | | |
| Aminoethylsulfonic acid | 0.2 | | | | | | |
| Sodium cromoglycate | 0.1 | | | | | | 0.1 |
| Sodium hyaluronate | | | 0.02 | | 0.02 | | 0.02 |
| Boric acid | 1 | 0.4 | 0.8 | | | 0.4 | 0.4 |
| Borax | 0.1 | | 0.06 | | | | |
| Sodium hydrogen phosphate | | | | 1 | 1 | | |
| Sodium dihydrogen phosphate | | | | 0.2 | | | |
| Potassium dihydrogen phosphate | | | | | 0.2 | | |
| EDTA | 0.1 | 0.002 | 0.002 | 0.002 | 0.002 | 0.002 | 0.002 |
| Trometamol | 0.1 | 0.1 | 0.1 | 0.1 | | | |
| Sodium chloride | 0.2 | | 0.6 | | | | |
| Potassium chloride | | 0.6 | | 0.6 | | | |
| Sodium hydrogencarbonate | | | | | | | 0.05 |
| Sodium citrate | | | | | | | 0.05 |
| Polyvinyl alcohol | | | | 0.5 | | | |
| Polyvinylpyrrolidone | 0.25 | | 0.25 | | | | |
| Hydroxyethyl cellulose | | | | | | 0.5 | |
| Hydroxypropylmethyl cellulose | | | | | 0.1 | | 0.1 |
| Methyl cellulose | | | 0.1 | | | | |
| Glucose | | 0.05 | | | | | |
| Glycerine | | | | | 0.5 | | |
| D-Mannitol | | | | | | 0.1 | |
| Xylitol | | | | | | | 0.05 |
| Polyoxyethylene hardened castor oil 60 | | | | 0.1 | | | |
| Polysorbate 80 | | | | 0.1 | | | |
| Macrogol 4000 | | | | | 0.1 | | |
| Macrogol 6000 | | 0.01 | | | | | 0.1 |
| Alginic acid | | | 0.1 | | | | |
| Potassium sorbate | | | | | | 0.1 | 0.1 |
| Propylene glycol | 0.5 | 0.8 | 0.8 | 0.8 | 0.5 | 0.5 | 0.5 |
| l-menthol | 0.009 | 0.009 | 0.008 | 0.008 | 0.012 | 0.008 | 0.009 |
| dl-Camphor | 0.005 | 0.005 | 0.003 | | | 0.003 | 0.005 |
| d-Borneol | | | 0.002 | | 0.001 | | |
| *Eucalyptus* oil | | | | 0.002 | | | |
| pH adjuster (HCl/NaOH) | | | Appropriate amounts | | | | |
| Total | | | | 100.0 | | | |
| pH | 3.8 | 3.8 | 3.8 | 3.8 | 3.8 | 3.8 | 3.8 |
| Suppression of adsorption of a basic chemical substance | ⊚ | ⊚ | ⊚ | ⊚ | ⊚ | ⊚ | ⊚ |

TABLE 8

| Composition (w/v %) | Example 42 | 43 | 44 | 45 | 46 | 47 |
|---|---|---|---|---|---|---|
| Potassium/magnesium L-aspartates (mixture in equal amounts) | 0.1 | 0.1 | 0.1 | 0.1 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.02 | 0.02 | 0.01 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |

TABLE 8-continued

| Composition (w/v %) | Example 42 | 43 | 44 | 45 | 46 | 47 |
|---|---|---|---|---|---|---|
| Retinol palmitate | 0.01 | | | 0.005 | | |
| Pyridoxine hydrochloride | | 0.1 | 0.1 | | 0.1 | |
| Panthenol | | | | | | 0.1 |
| Tocopherol acetate | 0.05 | | | | | |
| Sodium cromoglycate | | | | | | 0.1 |
| Sodium hyaluronate | | 0.02 | | 0.02 | | 0.02 |
| Boric acid | 0.4 | 0.8 | | | 0.4 | 0.4 |
| Borax | | 0.06 | | | | |
| Sodium hydrogen phosphate | | | 1 | 1 | | |
| Sodium dihydrogen phosphate | | | 0.2 | | | |
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | 0.5 | | |
| Hydroxypropylmethyl cellulose | | | | 0.1 | | 0.1 |
| Methyl cellulose | | 0.1 | | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | | 0.1 | 0.1 |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | 0.002 | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 9

| Composition (w/v %) | Example 48 | 49 | 50 | 51 | 52 | 53 |
|---|---|---|---|---|---|---|
| L-glutamic acid | 0.1 | 0.1 | 0.1 | 0.1 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.02 | 0.02 | 0.01 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | |
| Zinc lactate | | | 0.1 | | | |
| Lysozyme chloride | | | | | 0.1 | |
| Retinol palmitate | 0.01 | | | 0.005 | | |

TABLE 9-continued

| Composition (w/v %) | Example 48 | 49 | 50 | 51 | 52 | 53 |
|---|---|---|---|---|---|---|
| Pyridoxine hydrochloride | | 0.1 | 0.1 | | 0.1 | |
| Panthenol | | | | | | 0.1 |
| Tocopherol acetate | 0.05 | | | | | |
| Sodium cromoglycate | | | | | | 0.1 |
| Sodium hyaluronate | | 0.02 | | 0.02 | | 0.02 |
| Boric acid | 0.4 | 0.8 | | | 0.4 | 0.4 |
| Borax | | 0.06 | | | | |
| Sodium hydrogen phosphate | | | 1 | 1 | | |
| Sodium dihydrogen phosphate | | | 0.2 | | | |
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | | 0.1 | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | | 0.1 | | |
| Polysorbate 80 | | | | | 0.1 | |
| Macrogol 4000 | | | | | | 0.1 |
| Macrogol 6000 | 0.01 | | | | | 0.1 |
| Alginic acid | | 0.1 | | | | |
| Potassium sorbate | | | | | 0.1 | 0.1 |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | 0.002 | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 10

| Composition (w/v %) | Example 54 | 55 | 56 | 57 | 58 | 59 |
|---|---|---|---|---|---|---|
| Sodium L-glutamate | 0.1 | 0.1 | 0.1 | 0.1 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.03 | 0.03 | 0.03 |
| Ephedrine hydrochloride | 0.05 | | | | | |
| Methylephedrine hydrochloride | | 0.05 | | | | |
| Phenylepherine hydrochloride | | | 0.001 | | | |
| Diphenhydramine hydrochloride | | | | 0.05 | | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | | 0.005 | | |
| Pyridoxine hydrochloride | | 0.1 | 0.1 | | 0.1 | |
| Panthenol | | | | | | 0.1 |
| Tocopherol acetate | 0.05 | | | | | |

TABLE 10-continued

| Composition (w/v %) | 54 | 55 | 56 | 57 | 58 | 59 |
|---|---|---|---|---|---|---|
| Sodium cromoglycate | | | | | | 0.1 |
| Sodium hyaluronate | | 0.02 | | 0.02 | | 0.02 |
| Boric acid | 0.4 | 0.8 | | | 0.4 | 0.4 |
| Borax | | | 0.06 | | | |
| Sodium hydrogen phosphate | | | | 1 | 1 | |
| Sodium dihydrogen phosphate | | | 0.2 | | | |
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | | 0.1 | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | 0.1 | 0.1 | |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| *Eucalyptus* oil | | | | 0.002 | | |
| pH adjuster (HCl/NaOH) | | | Appropriate amounts | | | |
| Total | | | 100.0 | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 11

| Composition (w/v %) | 60 | 61 | 62 | 63 | 64 | 65 |
|---|---|---|---|---|---|---|
| Epsilon aminocaproic acid | 0.1 | 0.1 | 0.1 | 0.1 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.03 | 0.03 | 0.03 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | 0.005 | | | |
| Pyridoxine hydrochloride | | 0.1 | | 0.1 | | 0.1 |
| Panthenol | | | | | | 0.1 |
| Tocopherol acetate | 0.05 | | | | | |
| Sodium cromoglycate | | | | | | 0.1 |
| Sodium hyaluronate | | 0.02 | | 0.02 | | 0.02 |

TABLE 11-continued

| Composition (w/v %) | 60 | 61 | 62 | 63 | 64 | 65 |
|---|---|---|---|---|---|---|
| Boric acid | 0.4 | 0.8 | | | 0.4 | 0.4 |
| Borax | | | 0.06 | | | |
| Sodium hydrogen phosphate | | | | 1 | 1 | |
| Sodium dihydrogen phosphate | | | 0.2 | | | |
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | | 0.5 | | |
| Polyvinylpyrrolidone | | | 0.25 | | | |
| Hydroxyethyl cellulose | | | | | 0.5 | |
| Hydroxypropylmethyl cellulose | | | | | 0.1 | 0.1 |
| Methyl cellulose | | | 0.1 | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | | 0.1 | | |
| Polysorbate 80 | | | | | 0.1 | |
| Macrogol 4000 | | | | | 0.1 | |
| Macrogol 6000 | 0.01 | | | | | 0.1 |
| Alginic acid | | 0.1 | | | | |
| Potassium sorbate | | | | | 0.1 | 0.1 |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| *Eucalyptus* oil | | | 0.002 | | | |
| pH adjuster (HCl/NaOH) | | | Appropriate amounts | | | |
| Total | | | 100.0 | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 12

| Composition (w/v %) | 66 | 67 | 68 | 69 | 70 | 71 |
|---|---|---|---|---|---|---|
| α-Cyclodextrin | 0.25 | 0.1 | 0.1 | 0.25 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.03 | 0.03 | 0.03 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | 0.005 | | | |
| Pyridoxine hydrochloride | | 0.1 | | 0.1 | | 0.1 |
| Panthenol | | | | | | 0.1 |
| Tocopherol acetate | 0.05 | | | | | |
| Sodium cromoglycate | | | | | | 0.1 |
| Sodium hyaluronate | | 0.02 | | 0.02 | | 0.02 |
| Boric acid | 0.4 | 0.8 | 0.4 | | | 0.4 |
| Borax | | | 0.06 | | | |

TABLE 12-continued

| Composition (w/v %) | Example 66 | 67 | 68 | 69 | 70 | 71 |
|---|---|---|---|---|---|---|
| Sodium hydrogen phosphate | | | | 1 | 1 | |
| Sodium dihydrogen phosphate | | | | | 0.2 | |
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | 0.1 | | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | 0.1 | 0.1 | |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | 0.002 | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 13

| Composition (w/v %) | Example 72 | 73 | 74 | 75 | 76 | 77 |
|---|---|---|---|---|---|---|
| β-Cyclodextrin | 0.25 | 0.1 | 0.1 | 0.25 | 0.1 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.03 | 0.03 | 0.03 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | 0.001 | | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | | 0.005 | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | | 0.005 | | |
| Pyridoxine hydrochloride | | 0.1 | 0.1 | | 0.1 | |
| Panthenol | | | | | | 0.1 |
| Tocopherol acetate | 0.05 | | | | | |
| Sodium cromoglycate | | | | | | 0.1 |
| Sodium hyaluronate | | | 0.02 | | 0.02 | 0.02 |
| Boric acid | 0.4 | 0.8 | 0.4 | | | 0.4 |
| Borax | | 0.06 | | | | |
| Sodium hydrogen phosphate | | | | 1 | 1 | |
| Sodium dihydrogen phosphate | | | | | 0.2 | |

TABLE 13-continued

| Composition (w/v %) | Example 72 | 73 | 74 | 75 | 76 | 77 |
|---|---|---|---|---|---|---|
| Potassium dihydrogen phosphate | | | | 0.2 | | |
| EDTA | 0.002 | 0.002 | 0.002 | 0.002 | 0.002 | 0.002 |
| Trometamol | 0.1 | 0.1 | 0.1 | | | |
| Sodium chloride | | 0.6 | | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | 0.5 | | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | 0.1 | | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | 0.1 | 0.1 | |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | 0.002 | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 14

| Composition (w/v %) | Example 78 | 79 | 80 | 81 | 82 | 83 |
|---|---|---|---|---|---|---|
| γ-Cyclodextrin | 0.25 | 0.1 | 0.1 | 0.5 | 0.25 | 0.1 |
| Sodium chondroitin sulfate | 0.5 | 0.5 | 0.5 | 0.5 | 0.5 | 0.5 |
| Chlorpheniramine maleate | 0.03 | 0.03 | 0.03 | 0.03 | 0.03 | 0.03 |
| Epinephrine hydrochloride | 0.001 | | | | | |
| Ephedrine hydrochloride | | 0.05 | | | | |
| Methylephedrine hydrochloride | | | 0.05 | | | |
| Phenylepherine hydrochloride | | | | | 0.001 | |
| Diphenhydramine hydrochloride | | | | | 0.05 | |
| Tetrahydrozoline hydrochloride | 0.005 | | 0.005 | | 0.005 | |
| Naphazoline hydrochloride | | 0.003 | | 0.003 | | 0.003 |
| Neostigmine methylsulfate | | 0.005 | | | | 0.005 |
| Allantoin | 0.1 | 0.1 | 0.1 | 0.1 | 0.1 | 0.1 |
| Zinc sulfate | 0.1 | 0.1 | | 0.1 | | 0.1 |
| Zinc lactate | | | 0.1 | | | |
| Lysozyme chloride | | | | | 0.1 | |
| Retinol palmitate | 0.01 | | | 0.005 | | |
| Pyridoxine hydrochloride | | 0.1 | 0.1 | | 0.1 | |
| Panthenol | | | | | | 0.1 |
| Tocopherol acetate | 0.05 | | | | | |
| Sodium cromoglycate | | | | | | 0.1 |
| Sodium hyaluronate | | | 0.02 | | 0.02 | 0.02 |
| Boric acid | 0.4 | 0.8 | 0.4 | | | 0.4 |
| Borax | | 0.06 | | | | |
| Sodium hydrogen phosphate | | | | 1 | 1 | |
| Sodium dihydrogen phosphate | | | | | 0.2 | |
| Potassium dihydrogen phosphate | | | | 0.2 | | |

TABLE 14-continued

| Composition (w/v %) | Example 78 | 79 | 80 | 81 | 82 | 83 |
|---|---|---|---|---|---|---|
| EDTA | 0.002 | 0.002 | 0.002 | 0.002 | 0.002 | 0.002 |
| Trometamol | 0.1 | 0.1 | 0.1 | | | |
| Sodium chloride | | | 0.6 | | | |
| Potassium chloride | 0.6 | | 0.6 | | | |
| Sodium hydrogencarbonate | | | | | | 0.05 |
| Sodium citrate | | | | | | 0.05 |
| Polyvinyl alcohol | | | | 0.5 | | |
| Polyvinylpyrrolidone | | 0.25 | | | | |
| Hydroxyethyl cellulose | | | | | 0.5 | |
| Hydroxypropylmethyl cellulose | | | | 0.1 | | 0.1 |
| Methyl cellulose | | 0.1 | | | | |
| Glucose | 0.05 | | | | | |
| Glycerine | | | | 0.5 | | |
| D-Mannitol | | | | | 0.1 | |
| Xylitol | | | | | | 0.05 |
| Polyoxyethylene hardened castor oil 60 | | | 0.1 | | | |
| Polysorbate 80 | | | | 0.1 | | |
| Macrogol 4000 | | | | | 0.1 | |
| Macrogol 6000 | 0.01 | | | | | 0.1 |
| Alginic acid | | 0.1 | | | | |
| Potassium sorbate | | | | 0.1 | 0.1 | |
| Propylene glycol | 0.8 | 0.8 | 0.8 | 0.5 | 0.5 | 0.5 |
| l-menthol | 0.009 | 0.008 | 0.008 | 0.012 | 0.008 | 0.009 |
| dl-Camphor | 0.005 | 0.003 | | | 0.003 | 0.005 |
| d-Borneol | | | 0.002 | 0.001 | | |
| Eucalyptus oil | | | | 0.002 | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 15

| Composition (w/v %) | Example 84 | 85 | 86 | 87 | 88 | 89 | 90 |
|---|---|---|---|---|---|---|---|
| Chlorpheniramine maleate | 0.03 | 0.03 | 0.03 | 0.03 | 0.03 | 0.03 | 0.03 |
| Pranoprofen | 0.05 | | | | | | |
| Diclofenac sodium | | 0.1 | | | | | |
| Allantoin | | | 0.1 | | | | |
| Ketotifen fumarate | | | | 0.05 | | | |
| Acitazanolast | | | | | 0.1 | | |
| Levocabastine hydrochloride | | | | | | 0.1 | |
| Amlexanox | | | | | | | 0.2 |
| Sodium glutamate | 0.03 | | | | | | 0.03 |
| Epsilon aminocaproic acid | | 0.03 | | | | | |
| Potassium L-aspartate | | | 0.03 | | | | |
| α-Cyclodextrin | | | | 0.03 | | | |
| β-Cyclodextrin | | | | | 0.03 | | |
| γ-Cyclodextrin | | | | | | 0.03 | |
| Sodium chondroitin sulfate | 0.5 | 0.5 | 0.5 | 0.5 | 0.5 | 0.5 | 0.5 |
| Retinol palmitate | 0.01 | | | 0.005 | | | 0.01 |
| Pyridoxine hydrochloride | | 0.1 | 0.1 | | 0.1 | | |
| Panthenol | | | | | | 0.1 | |
| Tocopherol acetate | 0.05 | | | | | | 0.05 |
| Sodium cromoglycate | | | | | | 0.1 | |
| Sodium hyaluronate | | 0.02 | | 0.02 | 0.02 | | |
| Boric acid | 0.2 | 0.2 | 0.2 | 0.2 | 0.2 | 0.2 | 0.2 |
| Borax | | | 0.01 | | | | |
| EDTA | 0.002 | 0.002 | 0.002 | 0.002 | 0.002 | 0.002 | 0.002 |
| Trometamol | 0.002 | 0.002 | 0.002 | | | | 0.002 |
| Sodium chloride | | 0.3 | | | | | |
| Potassium chloride | 0.3 | | | 0.3 | | | 0.3 |

TABLE 15-continued

| Composition (w/v %) | Example 84 | 85 | 86 | 87 | 88 | 89 | 90 |
|---|---|---|---|---|---|---|---|
| Sodium hydrogencarbonate | | | | | | 0.01 | |
| Sodium citrate | | | | | | 0.01 | |
| Polyvinyl alcohol | | | 0.1 | | | | |
| Polyvinylpyrrolidone | | 0.25 | | | | | |
| Hydroxyethyl cellulose | | | | | 0.5 | | |
| Hydroxypropylmethyl cellulose | | | | 0.1 | | 0.1 | |
| Methyl cellulose | | | 0.1 | | | | |
| Glucose | 0.05 | | | | | | 0.05 |
| Glycerine | | | | 0.5 | | | |
| D-Mannitol | | | | | 0.1 | | |
| Xylitol | | | | | | 0.05 | |
| Polyoxyethylene hardened castor oil 60 | | | 0.1 | | | | |
| Polysorbate 80 | | | | 0.1 | | 0.1 | |
| Macrogol 4000 | | | | | 0.1 | | |
| Macrogol 6000 | 0.01 | | | | | 0.1 | 0.01 |
| Alginic acid | | 0.1 | | | | | |
| Potassium sorbate | | | | 0.1 | 0.1 | | |
| Propylene glycol | 0.8 | 0.8 | 0.8 | 0.5 | 0.5 | 0.5 | 0.8 |
| l-menthol | 0.009 | 0.008 | 0.008 | 0.012 | 0.008 | 0.009 | 0.009 |
| dl-Camphor | 0.005 | 0.003 | | | 0.003 | 0.005 | 0.005 |
| d-Borneol | | 0.002 | | 0.001 | | | |
| Eucalyptus oil | | 0.002 | | | | | |
| pH adjuster (HCl/NaOH) | Appropriate amounts | | | | | | |
| Total | 100.0 | | | | | | |
| pH | 3.8 | 3.8 | 3.8 | 3.8 | 3.8 | 3.8 | 3.8 |
| Suppression of adsorption of a basic chemical substance | ◎ | ◎ | ◎ | ◎ | ◎ | ◎ | ◎ |

TABLE 16

| Composition (w/v %) | Example 91 | 92 | 93 | 94 | 95 | 96 |
|---|---|---|---|---|---|---|
| Chlorpheniramine maleate | 0.03 | 0.03 | 0.03 | 0.03 | 0.03 | 0.03 |
| Ibudilast | 0.01 | | | | | |
| Pemirolast potassium | | 0.1 | | | | |
| Lomefloxacin hydrochloride | | | 0.1 | | | |
| Ofloxacin | | | | 0.1 | | |
| Norfloxacin | | | | | 0.1 | |
| Gentamicin sulfate | | | | | | 0.1 |
| Epsilon aminocaproic acid | 0.03 | | | | | |
| Potassium L-aspartate | | 0.03 | | | | 0.03 |
| α-Cyclodextrin | | | 0.03 | | | |
| β-Cyclodextrin | | | | 0.03 | | |
| γ-Cyclodextrin | | | | | 0.03 | |
| Sodium chondroitin sulfate | 0.5 | 0.5 | 0.5 | 0.5 | 0.5 | 0.5 |
| Retinol palmitate | | | 0.005 | | | 0.01 |
| Pyridoxine hydrochloride | 0.1 | 0.1 | | 0.1 | | |
| Panthenol | | | | | 0.1 | |
| Tocopherol acetate | | | | | | 0.05 |
| Sodium cromoglycate | | | | | 0.1 | |
| Sodium hyaluronate | 0.02 | | 0.02 | | 0.02 | |
| Boric acid | 0.2 | 0.2 | 0.2 | 0.2 | 0.2 | 0.2 |
| Borax | 0.01 | | | | | |
| EDTA | 0.002 | 0.002 | 0.002 | 0.002 | 0.002 | 0.002 |
| Trometamol | 0.002 | 0.002 | | | | 0.002 |
| Sodium chloride | 0.3 | | | | | |
| Potassium chloride | | | 0.3 | | | 0.3 |
| Sodium hydrogencarbonate | | | | | 0.01 | |
| Sodium citrate | | | | | 0.01 | |
| Polyvinyl alcohol | | | 0.5 | | | |
| Polyvinylpyrrolidone | | 0.25 | | | | |
| Hydroxyethyl cellulose | | | | 0.5 | | |
| Hydroxypropylmethyl cellulose | | | | 0.1 | | 0.1 |
| Methyl cellulose | | 0.1 | | | | |

TABLE 16-continued

| Composition (w/v %) | Example 91 | 92 | 93 | 94 | 95 | 96 |
|---|---|---|---|---|---|---|
| Glucose | | | | | | 0.05 |
| Glycerine | | | 0.5 | | | |
| D-Mannitol | | | | 0.1 | | |
| Xylitol | | | | | 0.05 | |
| Polyoxyethylene hardened castor oil 60 | | 0.1 | | | | |
| Polysorbate 80 | | | | 0.1 | | |
| Macrogol 4000 | | | | 0.1 | | |
| Macrogol 6000 | | | | | 0.1 | 0.01 |
| Alginic acid | 0.1 | | | | | |
| Potassium sorbate | | | 0.1 | 0.1 | | |
| Propylene glycol | 0.8 | 0.8 | 0.5 | 0.5 | 0.5 | 0.8 |
| l-menthol | 0.008 | 0.008 | 0.012 | 0.008 | 0.009 | 0.009 |
| dl-Camphor | 0.003 | | | 0.003 | 0.005 | 0.005 |
| d-Borneol | 0.002 | | 0.001 | | | |
| *Eucalyptus* oil | | 0.002 | | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 17

| Composition (w/v %) | Example 97 | 98 | 99 | 100 | 101 | 102 |
|---|---|---|---|---|---|---|
| Chlorpheniramine maleate | 0.03 | 0.03 | 0.03 | 0.03 | 0.03 | 0.03 |
| Sisomycin sulfate | 0.1 | | | | | |
| Micromycin sulfate | | 0.1 | | | | |
| Oxybuprocaine hydrochloride | | | 0.05 | | | |
| Distigmine bromide | | | | 0.2 | | |
| Timolol maleate | | | | | 0.1 | |
| Carteolol hydrochloride | | | | | | 0.5 |
| Sodium glutamate | 0.03 | | 0.03 | | | 0.03 |
| Potassium L-aspartate | | 0.03 | | | | |
| α-Cyclodextrin | | | 0.03 | | | |
| β-Cyclodextrin | | | | 0.03 | | |
| γ-Cyclodextrin | | | | | 0.03 | |
| Sodium chondroitin sulfate | 0.5 | 0.5 | 0.5 | 0.5 | 0.5 | 0.5 |
| Retinol palmitate | 0.01 | | 0.005 | | | 0.01 |
| Pyridoxine hydrochloride | | 0.1 | | 0.1 | | |
| Panthenol | | | | | 0.1 | |
| Tocopherol acetate | 0.05 | | | | | 0.05 |
| Sodium cromoglycate | | | | | 0.1 | |
| Sodium hyaluronate | | | 0.02 | | | 0.02 |
| Boric acid | 0.2 | 0.2 | 0.2 | 0.2 | 0.2 | 0.2 |
| EDTA | 0.002 | 0.002 | 0.002 | 0.002 | 0.002 | 0.002 |
| Trometamol | 0.002 | 0.002 | | | | 0.002 |
| Potassium chloride | 0.3 | 0.3 | | | | 0.3 |
| Sodium hydrogencarbonate | | | | | 0.01 | |
| Sodium citrate | | | | | 0.01 | |
| Polyvinyl alcohol | | 0.5 | | | | |
| Hydroxyethyl cellulose | | | | 0.5 | | |
| Hydroxypropylmethyl cellulose | | | 0.1 | | 0.1 | |
| Methyl cellulose | | | | | | |
| Glucose | 0.05 | | | | | 0.05 |
| Glycerine | | | 0.5 | | | |
| D-Mannitol | | | | 0.1 | | |
| Xylitol | | | | | 0.05 | |
| Polyoxyethylene hardened castor oil 60 | | 0.1 | | | | |
| Polysorbate 80 | | | | 0.1 | | |
| Macrogol 4000 | | | | 0.1 | | |
| Macrogol 6000 | 0.01 | | | | 0.1 | 0.01 |
| Potassium sorbate | | | 0.1 | 0.1 | | |
| Propylene glycol | 0.8 | 0.8 | 0.5 | 0.5 | 0.5 | 0.8 |
| l-menthol | 0.009 | 0.008 | 0.012 | 0.008 | 0.009 | 0.009 |
| dl-Camphor | 0.005 | | | 0.003 | 0.005 | 0.005 |
| d-Borneol | | | 0.001 | | | |
| *Eucalyptus* oil | | 0.002 | | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

TABLE 18

| Composition (w/v %) | Example 103 | 104 | 105 | 106 | 107 | 108 |
|---|---|---|---|---|---|---|
| Chlorpheniramine maleate | 0.03 | 0.03 | 0.03 | 0.03 | 0.03 | 0.03 |
| Betaxolol hydrochloride | 0.1 | | | | | |
| Dipivefrine hydrochloride | | 0.05 | | | | |
| Pilocarpine hydrochloride | | | 0.5 | | | |
| Pirenoxine | | | | 0.005 | | |
| Cyclopentolate hydrochloride | | | | | 0.5 | |
| Tropicamide | | | | | | 0.2 |
| Sodium glutamate | | | | | | 0.03 |
| Epsilon aminocaproic acid | 0.03 | | | | | |
| Potassium L-aspartate | | 0.03 | | | | |
| α-Cyclodextrin | | | 0.03 | | | |
| β-Cyclodextrin | | | | 0.03 | | |
| γ-Cyclodextrin | | | | | 0.03 | |
| Sodium chondroitin sulfate | 0.5 | 0.5 | 0.5 | 0.5 | 0.5 | 0.5 |
| Retinol palmitate | | 0.005 | | | | 0.01 |
| Pyridoxine hydrochloride | 0.1 | 0.1 | | 0.1 | | |
| Panthenol | | | | | 0.1 | |
| Tocopherol acetate | | | | | | 0.05 |
| Sodium cromoglycate | | | | | 0.1 | |
| Sodium hyaluronate | 0.02 | | 0.02 | | | 0.02 |
| Boric acid | 0.2 | 0.2 | 0.2 | 0.2 | 0.2 | 0.2 |
| Borax | 0.01 | | | | | |
| EDTA | 0.002 | 0.002 | 0.002 | 0.002 | 0.002 | 0.002 |
| Trometamol | 0.002 | 0.002 | | | | 0.002 |
| Sodium chloride | 0.3 | | | | | |
| Potassium chloride | | 0.3 | | | | 0.3 |
| Sodium hydrogencarbonate | | | | | 0.01 | |
| Sodium citrate | | | | | 0.01 | |
| Polyvinyl alcohol | | 0.5 | | | | |
| Polyvinylpyrrolidone | 0.25 | | | | | |
| Hydroxyethyl cellulose | | | | 0.5 | | |
| Hydroxypropylmethyl cellulose | | | | 0.1 | | 0.1 |
| Methyl cellulose | 0.1 | | | | | |
| Glucose | | | | | | 0.05 |
| Glycerine | | | 0.5 | | | |
| D-Mannitol | | | | 0.1 | | |
| Xylitol | | | | | 0.05 | |
| Polyoxyethylene hardened castor oil 60 | | 0.1 | | | | |
| Polysorbate 80 | | | | 0.1 | | |
| Macrogol 4000 | | | | 0.1 | | |
| Macrogol 6000 | | | | | 0.1 | 0.01 |
| Alginic acid | 0.1 | | | | | |
| Potassium sorbate | | | 0.1 | 0.1 | | |
| Propylene glycol | 0.8 | 0.8 | 0.5 | 0.5 | 0.5 | 0.8 |
| l-menthol | 0.008 | 0.008 | 0.012 | 0.008 | 0.009 | 0.009 |
| dl-Camphor | 0.003 | | | 0.003 | 0.005 | 0.005 |
| d-Borneol | 0.002 | | 0.001 | | | |
| *Eucalyptus* oil | | 0.002 | | | | |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Suppression of adsorption of a basic chemical substance | ◎ | ◎ | ◎ | ◎ | ◎ | ◎ |

According to the results of the examples and comparative examples, it has been recognized that the compositions incorporate into the amino acids and salts thereof, acidic mucopolysaccharides and salts thereof and cyclodextrins suppress the adsorption of the basic chemical substances on the soft contact lenses.

The following ingredients in Tables 6 to 18 are those indicated below, respectively.

| | |
|---|---|
| Polyvinyl alcohol: | Gohsenol EG05 (made by Nippon Synthetic Chemical Co., Ltd.) |
| Polyvinylpyrrolidone: | Kollidon 90F (made by BASF Japan Ltd.) |
| Hydroxyethyl cellulose: | HEC CF-H (made by Sumitomo Seika Chemicals Co., Ltd.) |
| Hydroxypropylmethyl cellulose: | Metlose 65SH-400 (made by Shin-Etsu Chemical Co., Ltd.) |
| Methyl cellulose: | Metlose SM-25 (made by Shin-Etsu Chemical Co., Ltd.) |

TABLE 19

| | Example | | | | | Comparative Example |
|---|---|---|---|---|---|---|
| Composition (w/v %) | 109 | 110 | 111 | 112 | 113 | 5 |
| Chlorpheniramine maleate | 0.03 | 0.03 | 0.03 | 0.03 | 0.03 | 0.03 |
| Allantoin | 0.1 | 0.1 | 0.1 | 0.1 | 0.1 | 0.1 |
| Boric acid | 0.4 | 0.4 | 0.4 | 0.4 | 0.4 | 0.4 |
| EDTA | 0.003 | 0.003 | 0.003 | 0.003 | 0.003 | 0.003 |
| Potassium chloride | 0.6 | 0.6 | 0.6 | 0.6 | 0.6 | 0.6 |
| Sodium glutamate | 0.1 | 0.1 | 0.1 | 0.1 | 0.1 | 0.1 |
| Propylene glycol | 0.8 | 0.8 | 0.8 | 0.8 | 0.8 | 0.8 |
| l-menthol | 0.009 | 0.009 | 0.009 | 0.009 | 0.009 | 0.009 |
| d-Borneol | 0.001 | 0.001 | 0.001 | 0.001 | 0.001 | 0.001 |
| pH adjuster (HCl/NaOH) | Appropriate amounts | | | | | |
| Total | 100.0 | | | | | |
| pH | 4.8 | 4.5 | 4.0 | 3.8 | 3.6 | 2.5 |
| Usability | ◎ | ◎ | ◎ | ◎ | ◎ | X |
| Usability (rating) | 4.5 | 4.6 | 4.6 | 4.8 | 4.3 | 1.7 |
| Q (ml) | 12 | 13 | 12 | 12 | 12 | 12 |

TABLE 20

| | Example | | | | |
|---|---|---|---|---|---|
| Composition (w/v %) | 114 | 115 | 116 | 117 | 118 |
| Chlorpheniramine maleate | 0.03 | 0.03 | 0.03 | 0.03 | 0.03 |
| Allantoin | 0.1 | 0.1 | 0.1 | 0.1 | 0.1 |
| Boric acid | 0.4 | 0.4 | 0.4 | 0.4 | 0.4 |
| EDTA | 0.05 | 0.05 | 0.05 | 0.05 | 0.05 |
| Potassium chloride | 0.1 | 0.1 | 0.1 | 0.1 | 0.1 |
| Sodium chloride | 0.3 | 0.3 | 0.3 | 0.3 | 0.3 |
| Sodium glutamate | 0.001 | 0.02 | 0.05 | 0.2 | 0.05 |
| Propylene glycol | 0.8 | 0.8 | 0.8 | 0.8 | 0.8 |
| l-menthol | 0.009 | 0.009 | 0.009 | 0.009 | |
| d-Borneol | 0.001 | 0.001 | 0.001 | 0.001 | |
| pH adjuster (HCl/NaOH) | Appropriate amounts | | | | |
| Total | 100.0 | | | | |
| pH | 3.8 | 3.8 | 3.8 | 3.8 | 3.8 |
| Usability | ◎ | ◎ | ◎ | ◎ | ○ |
| Usability (rating) | 4.7 | 4.6 | 4.7 | 4.1 | 3.2 |
| Q (ml) | 5 | 5 | 6 | 18 | 6 |

TABLE 21

| | Example | | | | | | | |
|---|---|---|---|---|---|---|---|---|
| Composition (w/v %) | 119 | 120 | 121 | 122 | 123 | 124 | 125 | 126 |
| Chlorpheniramine maleate | 0.03 | 0.03 | 0.03 | 0.03 | 0.03 | 0.03 | 0.03 | 0.03 |
| Boric acid | 0.4 | 0.4 | 0.4 | 0.4 | 0.4 | 0.4 | 0.4 | 0.4 |
| EDTA | 0.05 | 0.05 | 0.05 | 0.05 | 0.05 | 0.05 | 0.05 | 0.05 |
| Potassium chloride | 0.6 | 0.6 | 0.6 | 0.6 | 0.6 | 0.6 | 0.6 | 0.6 |
| Sodium chloride | 0.3 | 0.3 | 0.3 | 0.3 | 0.3 | 0.3 | 0.3 | 0.3 |
| Sodium glutamate | | | | | 0.05 | 0.05 | | |
| Potassium L-aspartate | 0.05 | | | | | 0.05 | 005 | |
| Epsilon aminocaproic acid | | 0.05 | | | | | | |
| Sodium chondroitin sulfate | | | 0.05 | | 0.05 | | | 0.05 |

TABLE 21-continued

| Composition (w/v %) | Example 119 | 120 | 121 | 122 | 123 | 124 | 125 | 126 |
|---|---|---|---|---|---|---|---|---|
| α-Cyclodextrin | | | | 0.05 | | | | |
| Sodium hyaluronate | | | | | | | | 0.05 |
| Propylene glycol | 0.8 | 0.8 | 0.8 | 0.8 | 0.8 | 0.8 | 0.8 | 0.8 |
| l-menthol | 0.009 | 0.009 | 0.009 | 0.009 | 0.009 | 0.009 | 0.009 | 0.009 |
| dl-Camphor | 0.001 | 0.001 | 0.001 | 0.001 | 0.001 | 0.001 | 0.001 | 0.001 |
| pH adjuster (HCl/NaOH) | Appropriate amounts | | | | | | | |
| Total | 100.0 | | | | | | | |
| pH | 3.8 | 3.8 | 3.8 | 3.8 | 3.8 | 3.8 | 3.8 | 3.8 |
| Usability | ○ | ○ | ◎ | ◎ | ◎ | ◎ | ◎ | ◎ |
| Usability (rating) | 3.9 | 3.8 | 4.8 | 4.9 | 4.5 | 4.6 | 4.8 | 4.7 |
| Q (ml) | 5 | 6 | 5 | 5 | 6 | 10 | 7 | 5 |

TABLE 22

| Composition (w/v %) | Example 127 | 128 | 129 | 130 | 131 | Comparative Example 6 |
|---|---|---|---|---|---|---|
| Chlorpheniramine maleate | 0.03 | 0.03 | 0.03 | 0.03 | 0.03 | 0.03 |
| Allantoin | 0.1 | 0.1 | 0.1 | 0.1 | 0.1 | 0.1 |
| Sodium chondroitin sulfate | 0.5 | 0.5 | 0.5 | 0.5 | 0.5 | 0.5 |
| Trometamol | 0.003 | 0.003 | 0.003 | 0.003 | 0.003 | 0.003 |
| Boric acid | 0.2 | 0.2 | 0.2 | 0.2 | 0.2 | 0.2 |
| EDTA | 0.003 | 0.003 | 0.003 | 0.003 | 0.003 | 0.003 |
| Potassium chloride | 0.1 | 0.1 | 0.1 | 0.1 | 0.1 | 0.1 |
| Sodium chloride | 0.3 | 0.3 | 0.3 | 0.3 | 0.3 | 0.3 |
| Propylene glycol | 0.8 | 0.8 | 0.8 | 0.8 | 0.8 | 0.8 |
| l-menthol | 0.009 | 0.009 | 0.009 | 0.009 | 0.009 | 0.009 |
| d-Borneol | 0.001 | 0.001 | 0.001 | 0.001 | 0.001 | 0.001 |
| pH adjuster (HCl/NaOH) | Appropriate amounts | | | | | |
| Total | 100.0 | | | | | |
| pH | 4.8 | 4.5 | 4.0 | 3.8 | 3.6 | 2.5 |
| Usability | ◎ | ◎ | ◎ | ◎ | ◎ | X |
| Usability (rating) | 4.4 | 4.6 | 4.4 | 4.5 | 4.2 | 1.7 |
| Q (ml) | 12 | 11 | 12 | 12 | 12 | 12 |

TABLE 23

| Composition (w/v %) | Example 132 | 133 | 134 | 135 | 136 | 137 |
|---|---|---|---|---|---|---|
| Chlorpheniramine maleate | 0.03 | 0.03 | 0.03 | 0.03 | 0.03 | 0.03 |
| Allantoin | 0.1 | 0.1 | 0.1 | 0.1 | 0.1 | 0.1 |
| Sodium chondroitin sulfate | 0.001 | 0.02 | 0.05 | 0.2 | 0.5 | 1 |
| Boric acid | 0.2 | 0.2 | 0.2 | 0.2 | 0.2 | 0.2 |
| EDTA | 0.05 | 0.05 | 0.05 | 0.05 | 0.05 | 0.05 |
| Potassium chloride | 0.1 | 0.1 | 0.1 | 0.1 | 0.1 | 0.1 |
| Sodium chloride | 0.3 | 0.3 | 0.3 | 0.3 | 0.3 | 0.3 |
| Propylene glycol | 0.8 | 0.8 | 0.8 | 0.8 | 0.8 | 0.8 |
| l-menthol | 0.009 | 0.009 | 0.009 | 0.009 | 0.009 | 0.009 |
| d-Borneol | 0.001 | 0.001 | 0.001 | 0.001 | 0.001 | 0.001 |
| pH adjuster (HCl/NaOH) | Appropriate amounts | | | | | |
| Total | 100.0 | | | | | |
| pH | 3.8 | 3.8 | 3.8 | 3.8 | 3.8 | 3.8 |
| Usability (rating) | 4.6 | 4.5 | 4.2 | 4.5 | 4.2 | 4.1 |
| Usability | ◎ | ◎ | ◎ | ◎ | ◎ | ◎ |
| Q (ml) | 5 | 5.1 | 5.2 | 5.5 | 12 | 18 |

The invention claimed is:

1. A method for suppressing adsorption of a basic chemical substance on a soft contact lens comprising: incorporating (B) at least one compound selected from the group consisting of L-glutamic acid and salts thereof, epsilon-aminocaproic acid and salts thereof, L-aspartic acid and salts thereof, chondroitin sulfate, a chondroitin polysulfate, and hyaluronic acid and salts thereof into a composition suitable for soft contact lenses including (A) a basic chemical substance selected from the group consisting of naphazoline, phenylephrine, neostigmine, diphenhydramine, tetrahydrozoline, pranoprofen, allantoin, and salts thereof, and (C) sterilized purified water;

adjusting the pH of the composition including the components (A), (B) and (C) to 3.5 to 3.9, and adjusting a buffer power Q of the composition including the components (A), (B), and (C) to 5 to 18 ml, said Q being represented by the following equation:

$$Q = QHCl + QNaOH$$

wherein QHCl is an amount (ml) of 0.1 mol/l of HCl necessary for lowering 100 g of the composition to a pH of 3.5, and QNaOH is an amount (ml) of 0.1 mol/l of NaOH necessary for raising 100 g of the composition to a pH of 7.5, at the pH measuring temperature of 20° C.

2. A composition suitable for treating soft contact lenses, comprising:
(A) 0.001 to 1.0 w/v % of at least one basic chemical substance selected from the group consisting of naphazoline, phenylephrine, neostigmine, diphenhydramine, tetrahydrozoline, pranoprofen, allantoin, and salts thereof;

(B) at least one compound selected from the group consisting of L-glutamic acid and salts thereof, epsilon-aminocaproic acid and salts thereof; L-aspartic acid and salts thereof in an amount of 0.01 to 3 w/v %, chondroitin sulfate, a chondroitin polysulfate, hyaluronic acid and salts thereof in an amount of 0.01 to 1 w/v %, (C) sterilized purified water; and (D) 0.01 to 2 w/v % of a buffering agent suitable to maintain the pH of the composition at a pH of 3.5 to 3.9, and the 5 to 18 ml of the buffer power Q of the composition, said Q being represented by the following equation of 5 to 18 ml:

$$Q=QHCl+QNaOH$$

wherein QHCl is an amount (ml) of 0.1 mol/l of HCl necessary for lowering 100 g of the composition to a pH of 3.5, and QNaOH is an amount (ml) of 0.1 mol/l of NaOH necessary for raising 100 g of the composition to a pH of 7.5, at the pH measuring temperature of 20° C.

3. The composition for soft contact lenses according to claim 2, wherein the buffering agent is selected from the group consisting of boron-based buffering agents, acetic acid-based buffering agents, phosphoric acid-based buffering agents, carbonic acid-based buffering agents, citric acid-based buffering agents and trometamol.

4. The composition for soft contact lenses according to claim 2, wherein said composition is free of a preservative selected from the group consisting of benzalkonium chloride, benzethonium chloride, chlorhexidine gluconate, sorbic acid, potassium sorbate, chlorobutanol, and paraben.

5. The method for suppressing adsorption of a basic chemical substance on a soft contact lens according to claim 1, wherein the buffer power Q is 5 to 14 ml.

6. The composition for soft contact lenses according to claim 2, wherein the buffer power Q is 5 to 14 ml.

7. The method for suppressing adsorption of a basic chemical substance on a soft contact lens according to claim 1, wherein component (A) is at least one basic chemical substance selected from the group consisting of diphenhydramine, tetrahydrozoline, and salts thereof.

8. The method for suppressing adsorption of a basic chemical substance on a soft contact lens according to claim 1, wherein the composition further includes (D) at least one buffering agent selected from the group consisting of a boric acid buffer, an acetic acid buffer, a phosphoric acid buffer, a carbonic acid buffer, a citric acid buffer and trometamol.

9. The composition for soft contact lenses according to claim 2, wherein the component (A) is at least one basic chemical substance selected from the group consisting of diphenhydramine, tetrahydrozoline, and salts thereof.

10. The composition for soft contact lenses according to claim 2, wherein the composition is an ophthalmic solution, a solution for wearing contact lenses, a solution for removing contact lenses or a care agent for contact lenses.

11. The method for suppressing adsorption of a basic chemical substance on a soft contact lens according to claim 1, wherein the component (B) is selected from the group consisting of a chondroitin sulfate, a chondroitin polysulfate, hyaluronic acid and salts thereof.

12. The method for suppressing adsorption of a basic chemical substance on a soft contact lens according to claim 1, wherein the component (B) is selected from the group consisting of L-glutamic acid, epsilon-aminocaproic acid, L-aspartic acid and salts thereof.

13. The composition for soft contact lenses according to claim 2, wherein the component (B) is selected from the group consisting of a chondroitin sulfate, a chondroitin polysulfate, hyaluronic acid and salts thereof.

14. The composition for soft contact lenses according to claim 2, wherein the component (B) is selected from the group consisting of L-glutamic acid, epsilon-aminocaproic acid, L-aspartic acid and salts thereof.

* * * * *